United States Patent [19]
Dieken et al.

[11] Patent Number: 6,026,170
[45] Date of Patent: *Feb. 15, 2000

[54] ELECTRONIC STETHOSCOPE WITH IDEALIZED BELL AND IDEALIZED DIAPHRAGM MODES

[75] Inventors: Alan P. Dieken, Oakdale; Joel R. Dufresne, St. Paul; Daniel V. Hulse, Inver Grove Heights, all of Minn.

[73] Assignee: Minnesota Mining and Manufacturing Company, St. Paul, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/563,186

[22] Filed: Nov. 27, 1995

[51] Int. Cl.⁷ .................................................. A61B 7/04
[52] U.S. Cl. ........................... 381/67; 181/126; 181/131; 181/137; 128/715; D24/134
[58] Field of Search ................... 381/67; 181/126, 181/131, 137; 128/715; D24/134

[56] References Cited

U.S. PATENT DOCUMENTS

| | | | |
|---|---|---|---|
| D. 361,840 | 8/1995 | Savage et al. | D24/134 |
| D. 362,063 | 9/1995 | Savage et al. | D24/134 |
| 1,658,327 | 2/1928 | Dodge . | |
| 2,001,537 | 5/1935 | Mason | 181/24 |
| 2,340,714 | 2/1944 | Traver et al. | 75/51 |
| 2,699,465 | 1/1955 | Hamilton | 179/5 |
| 3,087,016 | 4/1963 | Dahl | 179/1 |
| 3,182,129 | 5/1965 | Clark et al. | 179/1 |
| 3,247,324 | 4/1966 | Cefaly et al. | 179/1 |
| 3,311,703 | 3/1967 | Grinstead | 179/1 |
| 3,455,293 | 7/1969 | Bethune | 128/2.05 |
| 3,525,810 | 8/1970 | Adler | 179/1 |
| 3,539,724 | 11/1970 | Keesee | 179/1 |
| 3,555,187 | 1/1971 | Rowley | 179/1 |
| 3,651,798 | 3/1972 | Egli et al. | 128/2.05 S |
| 3,772,478 | 11/1973 | McCabe et al. | 179/1 ST |
| 3,790,712 | 2/1974 | Andries | 179/1 ST |
| 3,846,585 | 11/1974 | Slosberg et al. | 179/1 ST |
| 3,858,005 | 12/1974 | Marshall et al. | 179/1 ST |
| 3,989,895 | 11/1976 | O'Daniel, Sr. | 179/1 ST |

(List continued on next page.)

FOREIGN PATENT DOCUMENTS

| | | | |
|---|---|---|---|
| 31 43 372 | 5/1983 | Germany . | |
| 91 07 532 | 5/1992 | Germany . | |
| 4100607 | 7/1992 | Germany | 381/67 |
| 93 19 257 | 2/1994 | Germany . | |
| 43 42 768 | 6/1994 | Germany . | |
| Wo 87/00415 | 1/1987 | WIPO . | |
| WO 87/02233 | 4/1987 | WIPO . | |
| WO 91/02487 | 3/1991 | WIPO . | |
| WO 94/13206 | 6/1994 | WIPO | A61B 7/04 |
| WO 96/06562 | 3/1996 | WIPO . | |

OTHER PUBLICATIONS

Pätzold, J., Kompendium Elektromedizin, Grundlagen Technik, Anwedugen. Berlin, pp. 36–50 (1976) [no English translation].

*Primary Examiner*—Curtis Kuntz
*Assistant Examiner*—Duc Nguyen
*Attorney, Agent, or Firm*—Gary L. Griswold; Kari H. Bartingale; Jeffrey J. Hohenshell

[57] ABSTRACT

An electronic stethoscope emulates the frequency response of a standard acoustical stethoscope in both bell and diaphragm modes, while providing additional features attainable only with an electronic stethoscope, such as signal amplification, noise reduction, wider bandwidth, and mode selection. The electronic stethoscope includes spectrally separate idealized diaphragm and idealized bell modes. The idealized diaphragm mode and the idealized bell mode each include emphasized passbands and de-emphasized passbands. The emphasized passbands are spectrally separate. In addition, the electronic stethoscope also includes a wideband mode, which permits the user to hear high frequency sounds such as those associated with mechanical heart valves, lung sounds, and the like.

15 Claims, 5 Drawing Sheets

U.S. PATENT DOCUMENTS

| | | | |
|---|---|---|---|
| 4,071,694 | 1/1978 | Pfeiffer | 179/1 ST |
| 4,072,822 | 2/1978 | Yamada | 179/1.5 T |
| 4,170,717 | 10/1979 | Walshe | 179/1 ST |
| 4,218,584 | 8/1980 | Attenburrow | 179/1 ST |
| 4,220,160 | 9/1980 | Kimball et al. | 128/715 |
| 4,254,302 | 3/1981 | Walshe | 179/1 ST |
| 4,302,627 | 11/1981 | Inoue | 179/1 ST |
| 4,377,727 | 3/1983 | Schwalbach | 179/1 ST |
| 4,401,125 | 8/1983 | Taylor et al. | 128/715 |
| 4,424,815 | 1/1984 | Kuntz | 128/715 |
| 4,438,772 | 3/1984 | Slavin | 128/715 |
| 4,476,436 | 10/1984 | Koizumi et al. | 330/10 |
| 4,498,188 | 2/1985 | Hofer | 381/67 |
| 4,528,690 | 7/1985 | Sedgwick | 381/67 |
| 4,534,058 | 8/1985 | Hower | 381/67 |
| 4,594,731 | 6/1986 | Lewkowicz | 381/67 |
| 4,598,417 | 7/1986 | Deno | 381/67 |
| 4,607,643 | 8/1986 | Bell et al. | 128/715 |
| 4,618,986 | 10/1986 | Hower | 381/67 |
| 4,647,866 | 3/1987 | Brown | 330/262 |
| 4,649,928 | 3/1987 | Samaras et al. | 128/672 |
| 4,672,975 | 6/1987 | Sirota | 128/715 |
| 4,701,830 | 10/1987 | Kato et al. | |
| 4,720,866 | 1/1988 | Elias et al. | 381/67 |
| 4,731,849 | 3/1988 | Bloomfield, III | 381/67 |
| 4,783,813 | 11/1988 | Kempka | 381/67 |
| 4,783,814 | 11/1988 | Foley | 381/67 |
| 4,792,145 | 12/1988 | Eisenberg et al. | 128/715 |
| 4,821,327 | 4/1989 | Furugard et al. | 381/67 |
| 4,917,107 | 4/1990 | Bell et al. | 128/715 |
| 4,972,841 | 11/1990 | Iguchi | 128/715 |
| 4,985,925 | 1/1991 | Langberg et al. | 381/72 |
| 4,991,581 | 2/1991 | Andries | 128/715 |
| 5,003,605 | 3/1991 | Phillipps et al. | 381/67 |
| 5,010,889 | 4/1991 | Bredesen et al. | 128/715 |
| 5,022,405 | 6/1991 | Hök et al. | 128/715 |
| 5,025,809 | 6/1991 | Johnson et al. | 128/715 |
| 5,036,543 | 7/1991 | Ueno | 381/94 |
| 5,172,358 | 12/1992 | Kimura | 369/48 |
| 5,347,583 | 9/1994 | Dieken et al. | 381/67 |
| 5,367,575 | 11/1994 | Dieken et al. | 381/67 |
| 5,467,775 | 11/1995 | Callahan et al. | 381/67 |
| 5,492,129 | 2/1996 | Greenberger | 128/715 |
| 5,550,902 | 8/1996 | Abbruscato | |
| 5,602,924 | 2/1997 | Durand et al. | 381/67 |

ELECTRONIC STETHOSCOPE WITH IDEALIZED BELL AND IDEALIZED DIAPHRAGM MODES

BACKGROUND

Stethoscopes have long been used by physicians to monitor auscultatory sounds. Typically stethoscopes have been comprised of a head or chestpiece, a sound transmission mechanism and an earpiece assembly. The chestpiece is adapted to be placed near or against the skin, body, of a patient for gathering the auscultatory sounds. The sound transmission mechanism transmits the gathered sound to an earpiece, or a pair of earpieces called a binaural earpiece, where the physician or other health professional may monitor the sound.

Recently, some stethoscopes have utilized electronics for at least part of the sound processing path. In most of these devices, the auditory sound is picked up by a microphone usually located in a detection device which is similar to the chestpiece of a conventional acoustic stethoscope in external appearance. The electrical signal from the microphone is then processed electronically and is coupled to a speaker, or speakers, where the electrical signal is converted back into an auditory sound for reception by the physician. Of course, other electronic analysis or display of the auscultatory sound may be performed by the signal processor, in addition to the usual conversion back into an auditory sound.

The incorporation of electronic circuitry into the stethoscope has been a considerable design problem for the engineer. Electronic circuitry necessarily demands a supply of energy, most commonly a battery. Typically the batteries used in electronic stethoscopes have been of the small high energy density power cells such as those used in hearing aids, or selectively chosen and/or multiple units of more standard power cells that are operated within limited life cycles. Unfortunately, these specialized batteries are not widely available and are often expensive and difficult to dispose of.

In addition, although an electronic stethoscope allows for the provision of many desirable features, such as noise reduction, signal amplification, wider bandwidth, display of auscultatory sounds and selection of different frequency responses, the electronic scope has not gained wide acceptance due to the impression that electronic stethoscopes sound "different" or "electronic" or in some way distort the sound. Given that health care practitioners have long performed auscultation and based diagnosis on the sounds heard through a traditional acoustic stethoscope, the reluctance to change to something that sounds "different" is understandable.

Thus, there is a need in the art for an electronic stethoscope which sounds more like the traditional acoustic stethoscope but which has the additional desirable features which only an electronic stethoscope can provide.

SUMMARY

The present electronic stethoscope is designed to emulate the frequency response of a standard acoustical stethoscope in both bell and diaphragm modes, while providing additional features attainable only with an electronic stethoscope, such as signal amplification, noise reduction, wider bandwidth, and rapid mode selection.

The electronic stethoscope includes an idealized diaphragm mode and an idealized bell mode. The idealized diaphragm mode and the idealized bell mode each include emphasized passbands that are spectrally separate. Each of the idealized diaphragm and idealized bell modes can also include a de-emphasized passband. In addition, the electronic stethoscope can also include a wideband mode. The wideband mode permits the user to hear high frequency sounds such as those associated with mechanical heart valves or some lung sounds.

The spectral separation of the idealized bell and diaphragm modes allows the user to more easily hear and distinguish between different sounds of interest. The spectral separation of the emphasized frequencies reduces masking of high frequency sounds by low frequency sounds in the diaphragm mode, and reduces masking of low frequency sounds by high frequency sounds in the bell mode. Spectral separation with preservation of the de-emphasized frequencies of the idealized diaphragm and idealized bell modes allows the user to more easily hear, differentiate and identify different body sounds, and also gives the overall impression that the electronnic stethoscope emulates the sound quality of a good acoustic stethoscope.

BRIEF DESCRIPTION OF THE DRAWINGS

In the drawings, where like numerals refer to like elements throughout the several views.

DETAILED DESCRIPTION

Electronic stethoscopes should provide acoustic response at least equal to their conventional acoustic counterparts. Electronic stethoscopes should also be similar to the weight, feel and ease of use of their conventional acoustic counterparts. In order for the physician to gain the most advantageous use of the stethoscope, the stethoscope should provide the highest possible clarity of auscultatory sound from the patients body, as well as provide the greatest possible isolation from all extraneous sounds. In addition, electronic stethoscopes must offer sound isolation from the surroundings in which the stethoscope is used.

Figure 1:
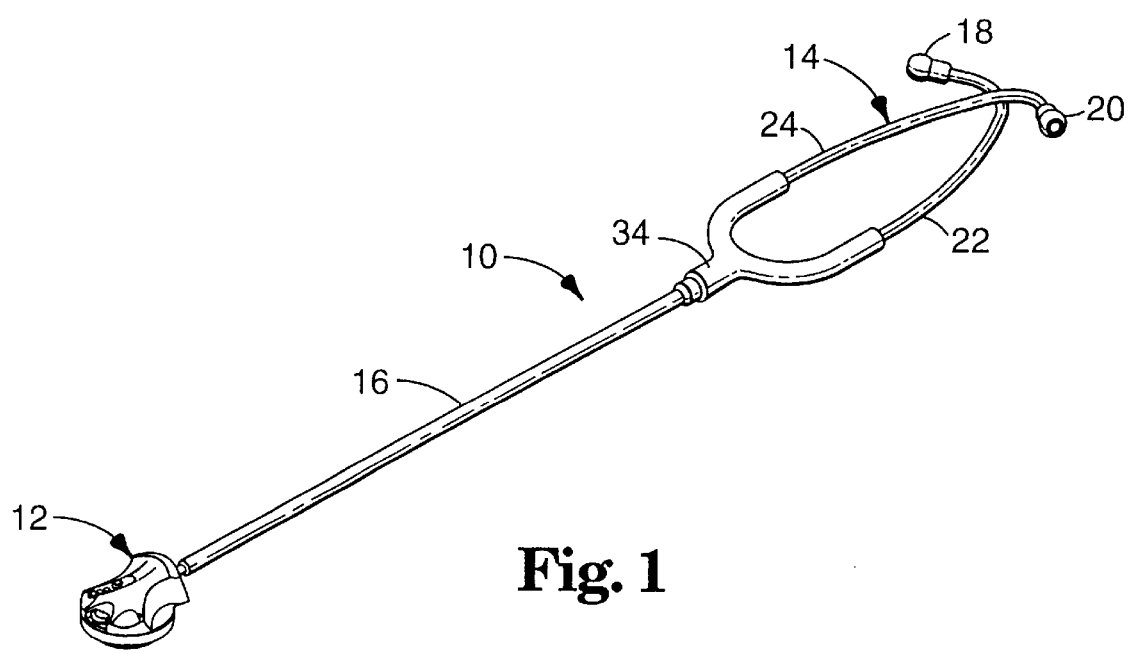
FIG. 1 shows the electronic stethoscope.

Electronic stethoscope 10 illustrated in FIG. 1 consists of a chestpiece 12, or stethoscope head, a headset 14 and a connecting tube 16. The binaural assembly 14 has two eartips 18 and 20 adapted to fit in the ear of a user, typically a physician or other medical professional. Tubes 22 and 24 are acoustically coupled to eartips 18 and 20, respectively. The eartips 18 and 20 effectively seal in the ear canal of the user to exclude ambient noise. Enclosure 34, located at juncture of tubes 22 and 24 with connecting tube 16, provides a location for a speaker (not shown). The speaker transforms the auscultatory sounds which are picked up by chestpiece 12 and transduced into and processed in the electrical domain back to the acoustic domain where tubes 22 and 24 transmit the acoustic sounds to eartips 18 and 20, respectively.

Figure 2:
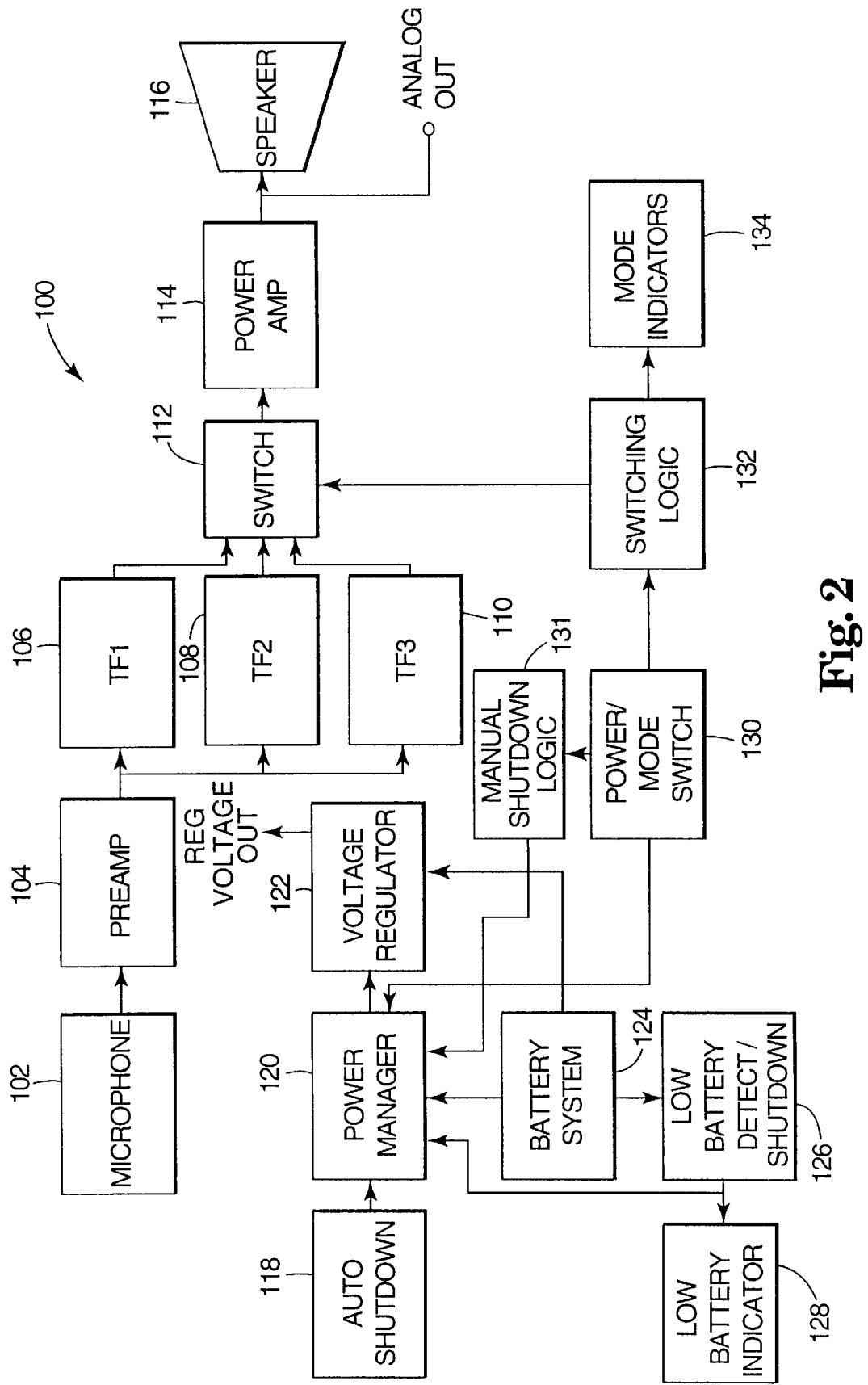
FIG. 2 shows a simplified block diagram of the preferred electronic stethoscope.

The preferred sound transmission system of stethoscope 10 is electronic. A simplified block diagram of the electronic sound transmission system 100 is illustrated in FIG. 2. The sound transmission system 100 includes at least one microphone 102 which acts as an acoustical transducer to receive auscultatory sounds from the body and transform the auscultatory sounds into an electrical signal. In an alternate embodiment, the stethoscope could include two or more microphones, although the system will be described with one microphone for purposes of illustration. This electrical signal is amplified and filtered by preamp/high pass filter 104. The preferred embodiment of the present electronic stethoscope is designed to emulate the frequency response of a standard acoustical stethoscope in both bell and diaphragm modes, while providing additional features attainable only with an electronic stethoscope, such as signal amplification, noise reduction, wider bandwidth, and mode selection. In the preferred embodiment, filters TF1 106, TF2 108 and TF3 110, permit selection between three different modes of operation of the electronic stethoscope. Additional filters and/or modes could be added without departing from the scope of the present invention. Emulation of the frequency response of a standard acoustical stethoscope is achieved with filters TF2 108 and TF3 110. Filter TF2 108 emulates the diaphragm mode of a standard acoustical stethoscope, while filter TF3 110 emulates the bell mode of a standard acoustical stethoscope. Filter TF1 106 provides a wideband frequency response which allows a user to hear a broad range of frequencies, including high frequency sounds such as those produced by mechanical heart valves and the like. These sounds can occur in a frequency range that is not audible with most acoustic stethoscopes.

Power/mode switch 130 provides for both power on of the circuitry and for mode selection in a single switch. Mode indicators 134 provide visual indication to the user as to the current operational mode of the stethoscope. Switching logic 132 is connected to power/mode switch 130 and controls electronic switch 112 which in turn determines which filter is being used to form the output to the user. Power amplifier 114 receives the filtered signal and the signal is output to the user via speaker 116. It shall be understood that embodiments in which speaker 116 includes one, two or more speakers are within the scope of the present invention.

The stethoscope 100 is powered by a battery system 124, which is preferably a commonly available AAA battery, preferably alkaline. A low battery detection/shutdown circuit 126 monitors available battery power and indicates when the battery power is running low via low battery indicator 128. When the voltage on the battery is below a predetermined level (1 volt, for example) the low battery detection/shutdown circuit 126 removes power from the stethoscope.

To prolong battery system life, an automatic shut down circuit 118 automatically removes power from the stethoscope after it has not been used for a preselected period of time. In one embodiment, the automatic shutdown circuit removes power a preselected period of time after the stethoscope is powered on. Alternatively, the automatic shutdown circuit removes power a preselected period of time after the last time the mode changed. A voltage regulator 122 provides DC—DC conversion from the battery voltage to a higher voltage (preferably 3.0 volts) and regulates and filters the voltage provided to the stethoscope circuitry.

Figure 3A:
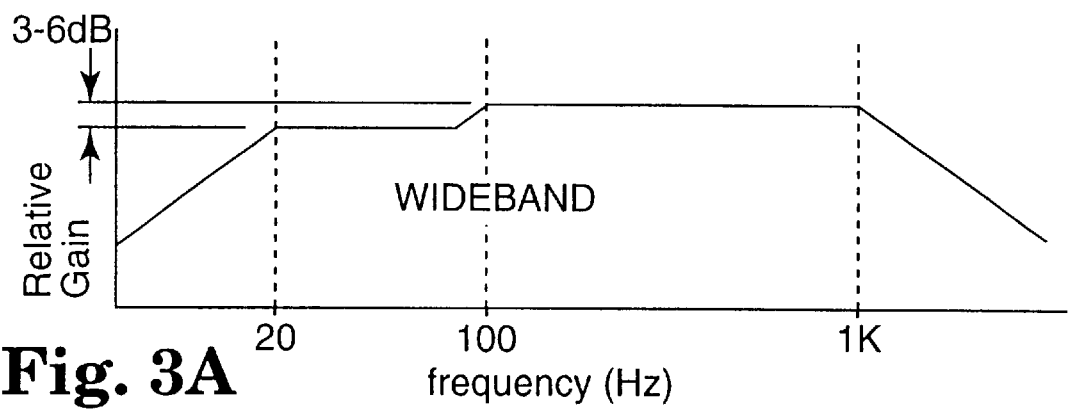
FIGS. 3A, 3B and 3C show the frequency responses of the preferred electronic stethoscope in the wideband, diaphragm and bell modes, respectively.
Figure 3B:
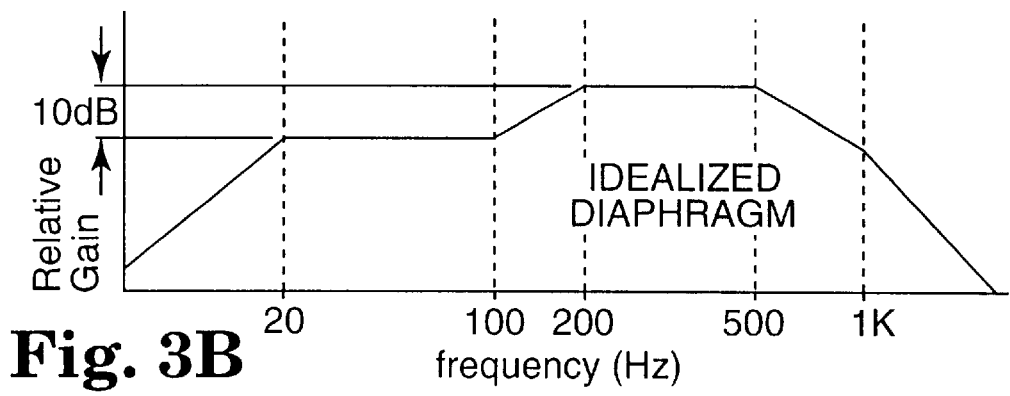
Figure 3C:
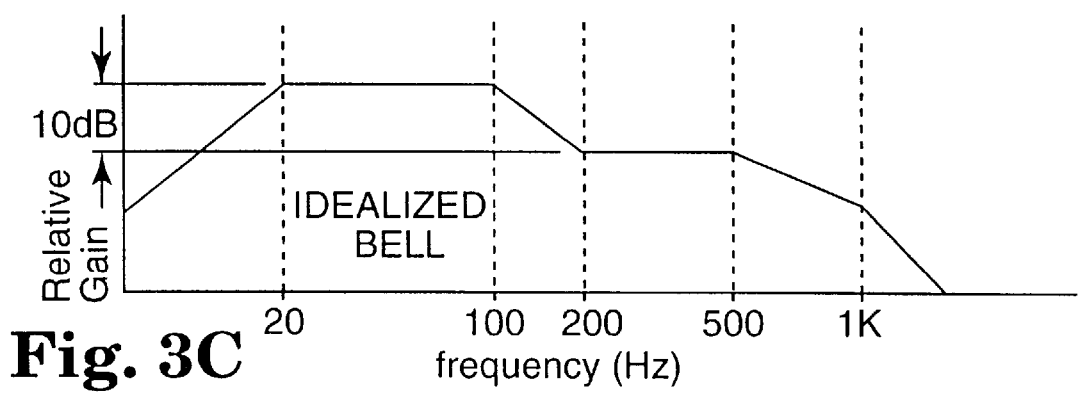

FIGS. 3A, 3B and 3C show the preferred frequency responses of the filters TF1 106, TF2 108 and TF3 110, respectively. The filters TF2 108 and TF3 110 provide an idealized diaphragm mode and an idealized bell mode, respectively. Filter TF1 106 provides an additional wideband mode.

The frequency response of idealized bell filter TF3 110 is shown in FIG. 3C. The frequency response of idealized diaphragm filter TF2 108 and is shown in FIG. 3B. As shown in FIGS. 3B and 3C and as described in more detail below, the frequency responses of the filters TF2 108 and TF3 110 are preferably spectrally separate. The frequency response of filter TF1 106 is shown in FIG. 3A, and provides a wideband frequency response. The wideband mode passes body sounds and other high frequency sounds within a wide spectral band.

The idealized bell and diaphragm modes should cover the ranges of frequencies of the biological sounds of interest. The frequency content of the cardiac, respiratory, fetal, Korotkoffs sounds, and other biological sounds of interest are present in an overall frequency range of about 20–2000 Hz. To allow the user to more easily hear and distinguish between sounds of interest of different frequencies, the idealized bell and diaphragm modes each emphasize a different portion of this overall frequency range.

In the preferred embodiment, the idealized diaphragm and idealized bell modes each have an overall passband which includes an emphasized passband and a de-emphasized passband. For the idealized diaphragm mode, the preferred emphasized passband is in the range of about 200–500 Hz, while the preferred de-emphasized passband is in the range of about 20–200 Hz. For the idealized bell mode, the preferred emphasized passband is in the range of about 20–100 Hz, while the preferred de-emphasized passband is in the range about of 100–500 Hz. To provide the distinction between the emphasized and de-emphasized passbands, the relative amplitude of the emphasized passband is preferably greater than that of the de-emphasized passband.

The idealized diaphragm mode emphasizes the high-frequency sounds while preserving some of the low-frequency sounds. In this way, the idealized diaphragm mode minimizes masking of high-frequency sounds (such as cardiac murmurs) by low-frequency sounds. As shown in FIG. 3B, the frequencies in the range of about 200–500 Hz are emphasized and the frequencies in the range of about 20–200 Hz are preserved but reduced in amplitude. To emphasize the frequencies in the range of about 200–500 Hz in the idealized diaphragm mode, the relative amplitude of the emphasized passband is sufficiently greater than that of the de-emphasized passband such that the resulting difference is perceptible to a user, and the attenuation of the de-emphasized passband is small enough such that the user can still hear the de-emphasized frequencies. For this purpose, a relative amplitude of the emphasized passband is in the range of about 5–15 dB greater than the de-emphasized passband is appropriate, with a preferred relative amplitude of about 10 dB.

Conversely, the idealized bell mode emphasizes the low-frequency sounds while preserving some of the high-frequency sounds. In this way, the idealized bell mode supports medical auscultation needs by minimizing psychoacoustic "masking" of low-frequency sounds by other sounds present at higher frequencies. As shown in FIG. 3C, the frequencies in the range of about 20–100 Hz are emphasized, while the frequencies in the range of about 100–500 Hz are preserved but reduced in amplitude. To emphasize the frequencies in the range of about 20–100 Hz in the idealized bell mode, the relative amplitude of the emphasized passband is sufficiently greater than that of the de-emphasized passband such that the resulting difference is perceptible to a user, and the attenuation of the de-emphasized passband is small enough such that the user can still hear the de-emphasized frequencies. For this purpose, a relative amplitude of the emphasized passband is in the range of about 5–15 dB greater than the de-emphasized passband is appropriate, with a preferred relative amplitude of about 10 dB.

In both the idealized bell and idealized diaphragm modes, attenuation in the range of about 500–1000 Hz is about 12 dB/octave, and is about 18 dB/octave above 1000 Hz. Because the human ear is more sensitive at higher frequencies, the user can still hear sounds present at frequencies above 500 Hz in both the idealized bell and idealized diaphragm modes even though they have relatively greater attenuation. To eliminate contamination of the body sounds by other environmental sounds, such as low frequency hand tremor, external noise and electronic noise, the overall passband is restricted to about 20–1000 Hz in the idealized bell and idealized diaphragm modes, and about 20–2000 Hz in the wideband mode.

As shown in FIGS. 3B and 3C, the "cross-over" frequency of the idealized bell and idealized diaphragm frequency responses is in the range of about 100–200 Hz. A uniform, relative attenuation of 6–12 dB/octave in this range is preferred to suppress masking of diagnostically significant sounds by other simultaneous and spectrally-adjacent sounds.

The emphasized and de-emphasized passbands in the idealized diaphragm and idealized bell modes result in an electronic stethoscope in which the idealized bell and idealized diaphragm modes are spectrally separate. The spectral separation of the idealized bell and diaphragm modes allows the user to more easily hear and distinguish between different sounds of interest. The spectral separation of the emphasized frequencies with preservation of the de-emphasized frequencies of the idealized diaphragm and idealized bell modes permits the electronic stethoscope to give the overall impression that it preserves the sound quality of a good acoustic stethoscope, which generally are not narrow-band instruments. Reduced masking of the high or low frequency sounds provided by the idealized diaphragm and idealized bell modes, respectively, means better clarity for the sound of interest, leading to more effective screening and diagnosis.

The wideband mode of FIG. 3A preferably provides a wider sound band with similar gain across all frequencies in the passband, but with a slight (e.g., 3–5 dB de-emphasis below 100 Hz. The wideband mode provides a response that cannot be achieved in a traditional acoustic stethoscope, and thus allows the user to hear sounds, such as some high frequency sounds from artificial heart valves and the like, which cannot be heard with traditional acoustic stethoscopes. For initial screening functions, auscultation can begin in the wideband mode, with the ideal bell or diaphragm mode selected as the user determines the frequency range of most interest. In addition, the wideband mode may be preferred for use with an external computer-based data acquisition and display system. A data acquisition system permits software selection of different frequency responses and the ability to display and manipulate these different responses. Audio playback and manipulation is also possible. The wideband mode may be preferred for this use because it passes a wider bandwidth. It shall be understood, however, that a data acquisition system, display, audio playback, etc., can be used with any of the idealized diaphragm, idealized bell, and wideband modes.

The above described operational modes provide the physician with distinctly different and advantageous sound processing modes. The idealized bell and diaphragm modes are more spectrally separate than with traditional stethoscopes, allowing the user to more easily hear and distinguish different sounds of interest. Traditional acoustic stethoscopes typically lack a uniform relative attenuation outside of the bell/diaphragm cross-over band, due the presence of acoustic resonances. Also, the switch over between bell and diaphragm modes with traditional acoustic stethoscopes generally required gross hand movements to engage a pneumatic valve or to turn over the chestpiece. In contrast, the different transfer functions of this invention can be quickly selected with the simple and easily operable power/mode switch 130. Thus, no repositioning of the chestpiece is required to switch between bell and diaphragm modes. In addition, the wideband mode allows the user to hear a full presentation of body sounds, and is also desirable for use with a computerized data acquisition and display system, or with an amplifier and speaker system, for example. Finally, because filtering of the body sounds is performed electronically, the manufacturing process is much more precise and repeatable than earlier nonelectronic constructions.

Figure 4:
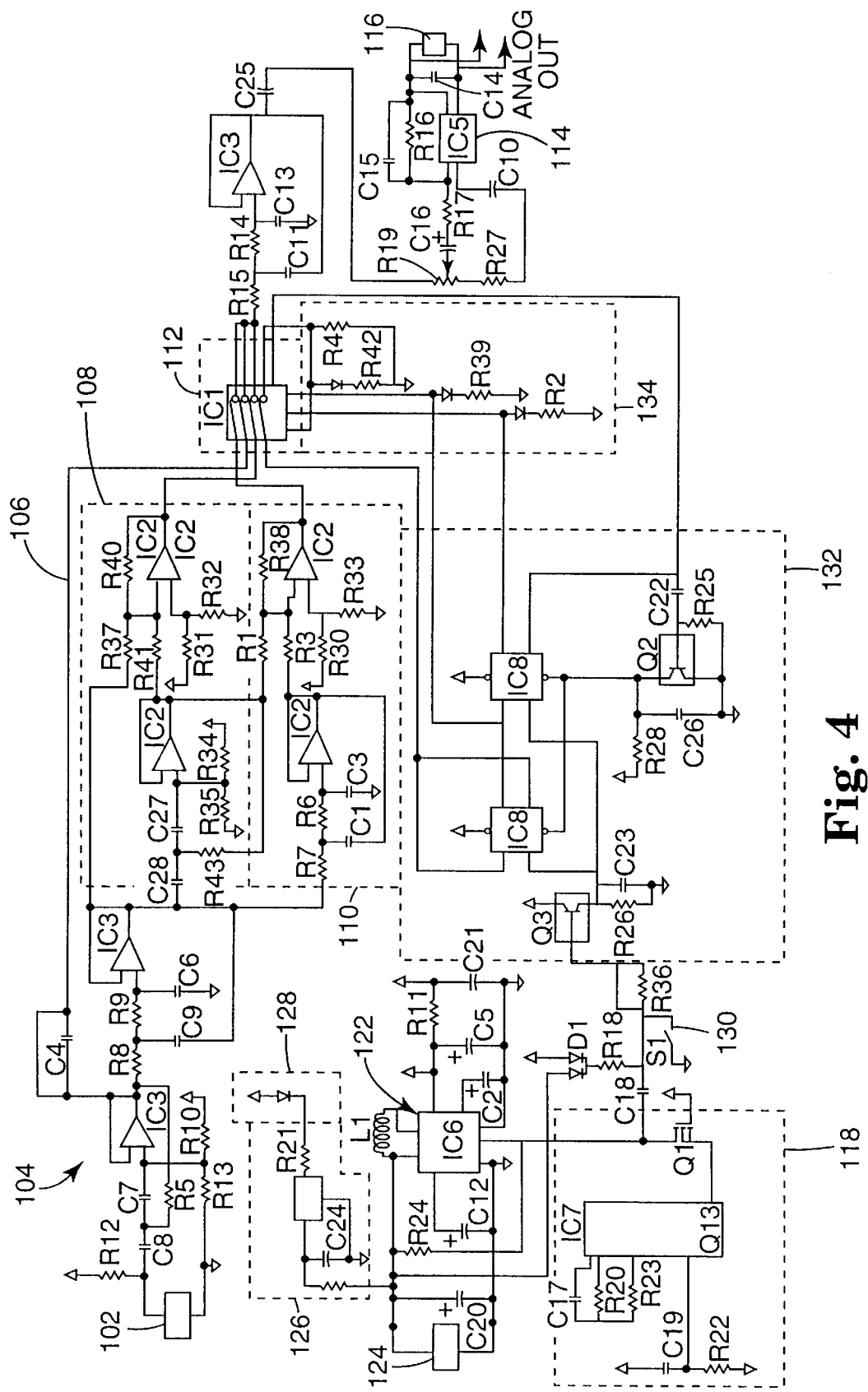
FIG. 4 shows a detailed electrical schematic diagram of the electronic stethoscope.

FIG. 4 shows a more detailed electrical schematic diagram of the electronic stethoscope. Electrical auscultatory sounds are received from the microphone 102 and are input into preamp/high pass filter 104, which consists of one section of operational amplifier IC3 and associated circuit components. The signal is then input into each of the filters TF1 106, TF2 108 and TF3 110. Capacitor C4 may be used to adjust the low frequency response of filter TF1 106, if desired. The filters can be realized with digital filters (ex. finite impulse response (FIR) filters), with digital signal processing (DSP) based filters, or with analog filter sections. In the preferred embodiment, filters TF2 108 and TF3 110 are both preferably implemented using second-order unity gain analog filters, and the signal from the second-order sections are combined by analog summing resistors (R37 and R41 for TF2 108, and R3 and R1 for TF3 110). Second-order unity gain analog filters are a particularly simple and cost-effective way to implement the desired transfer functions. Such unity-gain sections give very sharp cutoffs and also prevent unwanted "gain buildup" within long chains of filter elements, thereby reducing the likelihood of nonlinear saturation effects and distortion. The second-order filters minimize the presence of unwanted environmental noise (ex. voice, air-conditioner noise, etc.). Previously-used low-order filters (typically having only a single pole) were ineffective in eliminating "ambient noise" contamination. Also, previous filter circuits were aimed at achieving simple low-pass or high-pass effects, not the shaped transfer functions of this invention.

The overall frequency response of the stethoscope is also affected by other components such as the microphone, speaker, tubing, etc. To account for these effects which might undesirably affect the overall frequency response of the stethoscope, resistors R1, R3, R37 and R41 can be adjusted to compensate for variations caused by these other components. This adjustment results in an overall frequency response that closely approximates that of the filters.

Electronic switch 112 determines which of the three filter outputs are passed on to power amplifier 114. Electronic switch 112 is preferably implemented using a quad analog switch part number 74LV4066D available from Philips Corporation. Electronic switch 112 is controlled by sequential switching circuitry 132 which is in turn controlled by power/mode switch 130. Power-mode switch 130 is preferably a single push-button switch which, in combination with switching circuitry 132, allows the user to both power on the stethoscope, make mode selections, and manually turn off the stethoscope. Switching circuitry 132, which preferably includes dual D flip-flops IC8, transistors Q2 and Q3 and associated circuit components, tracks the depressions of power/mode switch 130 an provides appropriate sequential control to switch 112. Mode indicators 134 are preferably three high efficiency LEDs and associated circuit components each of which indicates one of the three possible operational modes, broadband, diaphragm or bell, as provided by the respective filter circuits TF1 106, TF2 108 or TF3 110, respectively.

The selected filter signal is passed through a 1000 Hz low pass filter to attenuate electronic noise and further reduce amplification of ambient noise. Power amplifier 114 is a low power audio amplifier which provides differential speaker outputs to the speaker 116. The power amplifier is preferably implemented using part number MC34119, "Low Power Audio Amplifier", available from Motorola Corporation.

The circuit is preferably powered using a single, commonly available AAA battery 124. Voltage regulator 122 provides DC—DC conversion of the power from the battery and also filters and regulates the voltage supplied to the circuit. In the preferred embodiment, voltage regulator 122 is an integrated circuit implemented using part number ML4890, "High Efficiency Low Ripple Boost Regulator", available from MicroLinear Corporation.

Voltage regulator 122 can operate over a wide range of voltage (energy) from the AAA battery, as low as 1.0 volts and possibly as low as 0.8 volts or a wide range of power availability caused by quality or shelf aging of the battery. The voltage regulator 122 supplies a constant voltage to the stethoscope such that sound quality and gain are not affected by the battery condition or voltage. Thus the instrument will perform effectively deep into the end-of-life of the battery power source. Voltage regulator 122 further functions as a buffer and filter which isolates switching noise and ripple noise emanating from the DC—DC converter, the battery, or the battery connection system and other noise that would adversely affect sound quality of the instrument.

In an alternate embodiment, voltage regulator 122 is implemented using a DC—DC step-up converter in series with a linear regulator. The DC—DC converter drives the linear regulator to reduce switching noise and ripple noise on the regulated output. This implementation effectively reduces the output noise of the voltage regulator 122 to 5 mV. The linear regulator thus supplies a constant, filtered voltage to the stethoscope such that sound quality and gain are not affected by battery condition or voltage.

Variable resistor R19 allows the user to adjust the volume of the resulting body sounds as heard through the stethoscope. Preferably, the middle range provided by variable resistor R19 is about unity gain (i.e., no amplification or attenuation of the incoming signal as compared to an acoustic stethoscope). This allows the electronic stethoscope to emulate the performance of an acoustic scope in that, in at least one volume setting, the output level is about equal to that of a traditional acoustic stethoscope. To further enhance the user's ability to hear the sounds of interest, the variable resistor R19 allows enhancement (amplification) or quieting (attenuation) of the amplitude and thus the volume of the signal output of speaker 116.

Low battery detection/shutoff circuit 126 is preferably implemented using a 1.15 volt voltage detector, part number S-8051ANR-NB, available from Seiko Corporation, which in combination with associated circuit components monitors the power output of the battery 124. When low power levels are detected (e.g., less than 1.15 volts in the preferred embodiment) the low battery indicator 128 is illuminated to inform the user that battery power is low and that the battery should soon be replaced. In an alternate embodiment, low battery detection/shutdown circuit 126 causes power to be removed from the stethoscope when the battery voltage is less than 1.0 volts.

Automatic shut down circuit 118 automatically removes power from the stethoscope after it has not been used for a preselected period of time. Counter IC7 is connected through transistor Q1 to power/mode switch 130. Each time the stethoscope is powered on, counter IC7 is reset, and begins to count up to a number equivalent to a preselected period of time. In an alternate embodiment, each time the power/mode switch 130 is depressed, counter IC7 is reset, and begins to count up to a number equivalent to a preselected period of time. In the preferred embodiment, the preselected period of time is about 3 minutes. To provide for the preferred preselected period of time, the counter output Q13 is connected through Q1 to the shutdown pin on voltage regulator 122. Once the counter counts up, the output Q13 goes high, thus causing voltage regulator 122 to shut down which removes power from the circuit.

Figure 5:
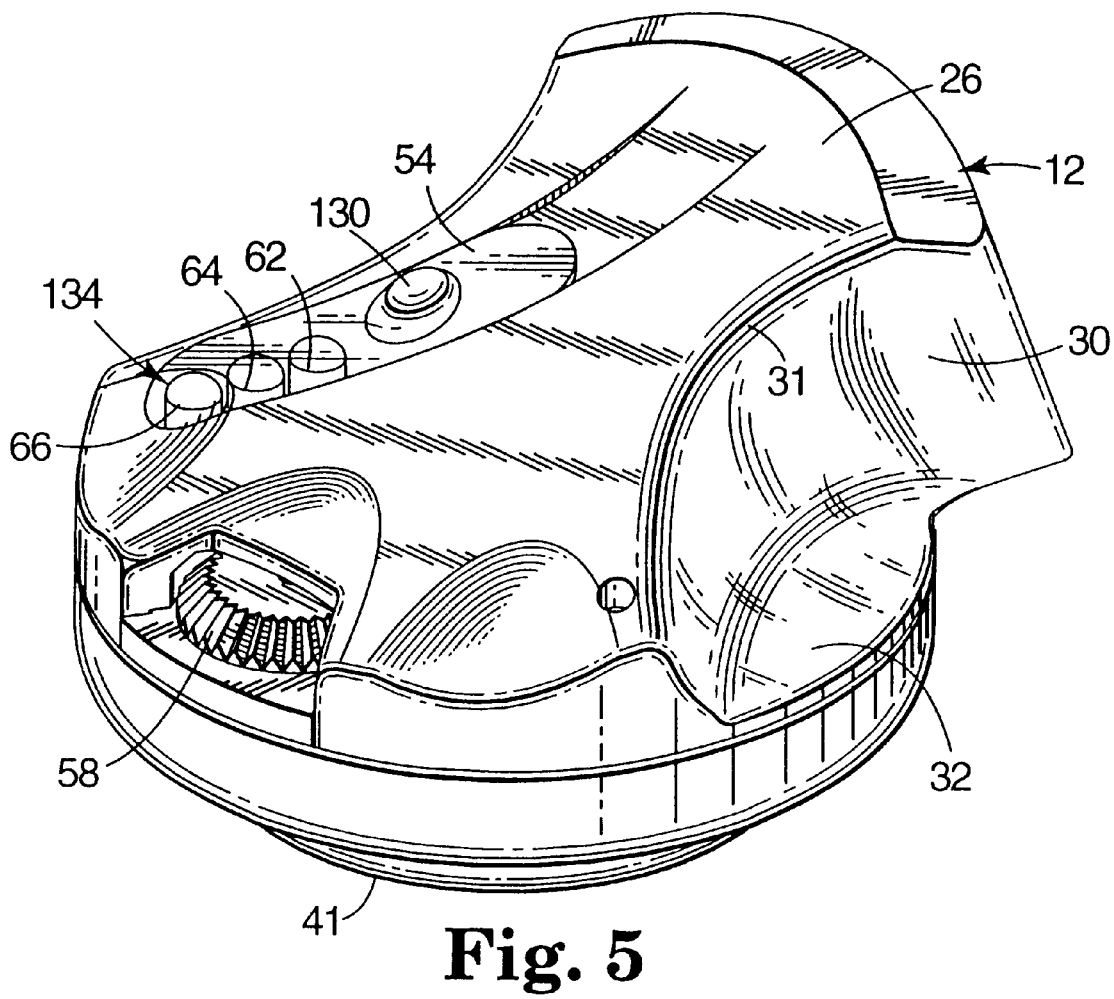
FIG. 5 shows the preferred chestpiece of the electronic stethoscope.

FIG. 5 shows the preferred stethoscope chestpiece 12. Chestpiece 12 preferably includes a raised center portion 26, indented gripping surfaces 28 and 30 which, in combination with protruding edges 28 and 31 and surface 32 form the indented impressions with which the user can securely, easily, and comfortably grasp the chestpiece using the thumb and one or more fingers. The preferred stethoscope chestpiece 12 is more completely described in copending and commonly assigned U.S. Patent Application, filed on even date herewith, and entitled "ERGONOMETRIC STETHOSCOPE CHESTPIECE", which is incorporated herein by reference.

The chestpiece 12 includes power/mode switch 130 and rotary control 58 for adjustment of the volume of the stethoscope as described above. Mode indicators 134 are preferably LEDs 62, 64, and 66. Alternatively, the mode indicator 134 is a small LCD or other type of display screen to further reduce power consumption. Each LED 62, 64 and 66 is associated with a different one of the preferred three operational modes, idealized diaphragm, idealized bell, and wideband. The LED 62, 64 or 66 associated with the current operational mode of the stethoscope is illuminated to provide visual indication to the user regarding the current operational mode of the stethoscope.

Although specific embodiments have been shown and described herein for purposes of illustration of exemplary embodiments, it will be understood by those of ordinary skill that a wide variety of alternate and/or equivalent implementations designed to achieve the same purposes may be substituted for the specific embodiments shown and described without departing from the scope of the present invention. It shall be understood that different hardware embodiments could be substituted for the specific embodiments shown and described herein. The circuit could be implemented on a single hybrid or monolithic integrated circuit, for example. Those of ordinary skill will readily appreciate that the present invention could be implemented in a wide variety of embodiments. This application is intended to cover any adaptations or variations of the preferred embodiments discussed herein. Therefore, it is intended that this invention be defined by the claims and the equivalents thereof.

We claim:

1. An electronic stethoscope, comprising:
microphone means for sensing sounds of interest produced within a patient's body;

filter means, adapted to receive the sounds of interest, for providing at least two spectrally separate operational modes, wherein the filter means includes:

bell mode means for receiving the sounds of interest and for producing therefrom a bell mode overall passband including a first emphasized passband from about 20–100 Hz and first de-emphasized passband from about 100–500 Hz, wherein a gain of the first emphasized passband is greater than a gain of the first de-emphasized passband by about 15 dB or less; and diaphragm mode means for receiving the sounds of interest and for producing therefrom a diaphragm ode overall passband including a second de-emphasized passband from about 20–200 Hz and a second emphasized passband from about 200–500 Hz, wherein a gain of the second emphasized passband is greater than a gain of the second de-emphasized passband by about 15 dB or less;

mode selection means for selecting between the operational modes; and speaker means for reproducing the filtered sounds for perception by a user.

2. The electronic stethoscope of claim 1 wherein the filter means adapted to provide the operational modes such that the electronic stethoscope has the sound of an acoustic stethoscope.

3. The electronic stethoscope of claim 1 further including a user adjustable volume control, wherein in at least one volume setting, the output level of the reproduced sounds is about equivalent to that of a traditional acoustic stethoscope.

4. The electronic stethoscope of claim 1 wherein the filter means is further for providing a wideband operational mode and wherein the filter means further includes wideband mode means for receiving the sounds of interest and for producing therefrom a wideband passband from about 20–2000 Hz.

5. The electronic stethoscope of claim 1 wherein the gain of the first emphasized passband is greater than the gain of the first de-emphasized passband by about 10 dB.

6. The electronic stethoscope of claim 1 wherein the gain of the second emphasized passband is greater than the gain of the second de-emphasized passband by about 10 dB.

7. An electronic stethoscope, comprising:

microphone means for sensing sounds of interest produced within a patient's body;

bell mode filter means adapted to receive the sounds of interest for providing an idealized bell mode overall passband filter from about 20–500 Hz when in a bell operational mode, the bell mode overall passband filter including at least a first emphasized passband from about 20–100 Hz and a first de-emphasized passband from about 100–500 Hz, wherein a gain of the first emphasized passband is greater than a gain of the first de-emphasized passband by about 15 dB or less; and diaphragm mode filter means adapted to receive the sounds of interest for providing an idealized diaphragm mode overall passband filter from about 20–500 Hz when in a diaphragm operational mode, the diaphragm mode overall passband filter including at least a second emphasized passband from about 200–500 Hz and a second de-emphasized passband from about 20–200 Hz, wherein a gain of the second emphasized passband is greater than a gain of the second de-emphasized passband by about 15 dB or less;

mode selection means for selecting between at least the bell and diaphragm operational modes; and speaker means for reproducing the filtered sounds for perception by a user.

8. The electronic stethoscope of claim 7 wherein the stethoscope further includes a wideband mode filter adapted to receive the sounds of interest, the wide band mode filter providing a wideband mode overall passband from about 20–2000 Hz.

9. The electronic stethoscope of claim 7 wherein the reproduced sounds are input into a computerized data acquisition system.

10. The electronic stethoscope of claim 7 wherein the stethoscope is powered by a AAA battery.

11. The electronic stethoscope of claim 7 wherein the filter means comprises digital filters.

12. The electronic stethoscope of claim 7 wherein the filter means comprises analog filters.

13. The electronic stethoscope of claim 7 further including mode indicating means for visually indicating the selected operational mode.

14. The electronic stethoscope of claim 7 further including a user adjustable volume control.

15. The electronic stethoscope of claim 14 wherein in at least one volume setting, the output level of the reproduced sounds is about equal to that of a traditional acoustic stethoscope.

* * * * *